United States Patent [19]
Robinson et al.

[11] Patent Number: 5,856,203
[45] Date of Patent: Jan. 5, 1999

[54] SENSOR DEVICE FOR SANDWICH ASSAY

[75] Inventors: Grenville Arthur Robinson, London; Janys Fletcher, Bagshot, both of United Kingdom

[73] Assignee: Applied Research Systems ARS Holding NV, Curacao, Netherlands

[21] Appl. No.: 663,243
[22] PCT Filed: Dec. 15, 1994
[86] PCT No.: PCT/GB94/02741
  § 371 Date: Jul. 17, 1996
  § 102(e) Date: Jul. 17, 1996
[87] PCT Pub. No.: WO95/16914
  PCT Pub. Date: Jun. 22, 1995

[30] Foreign Application Priority Data

Dec. 16, 1993 [GB] United Kingdom ............. 9325718

[51] Int. Cl.$^6$ ............. G01N 33/543; G01N 33/552
[52] U.S. Cl. ............. 436/518; 385/12; 385/129; 385/130; 422/55; 422/57; 422/58; 422/82.05; 422/82.08; 422/82.09; 422/82.11; 435/287.1; 435/287.2; 435/287.9; 435/288.7; 435/808; 436/164; 436/165; 436/172; 436/524; 436/527; 436/528; 436/531; 436/805
[58] Field of Search ............. 385/12, 129, 130; 422/55, 57, 58, 82.05, 82.08, 82.09, 82.11; 435/287.1, 287.2, 287.9, 288.7, 808; 436/164, 165, 172, 518, 524, 527, 528, 531, 805

[56] References Cited

U.S. PATENT DOCUMENTS

| | | | |
|---|---|---|---|
| 4,978,503 | 12/1990 | Shanks et al. | 422/58 |
| 5,141,868 | 8/1992 | Shanks et al. | 436/518 |
| 5,512,492 | 4/1996 | Herron et al. | 436/518 |
| 5,525,466 | 6/1996 | Slovacek et al. | 435/6 |

FOREIGN PATENT DOCUMENTS

| | | |
|---|---|---|
| 0422708 | 4/1991 | European Pat. Off. . |
| 9209892 | 6/1992 | WIPO . |
| 9325908 | 12/1993 | WIPO . |

*Primary Examiner*—Christopher L. Chin
*Attorney, Agent, or Firm*—Ostrolenk, Faber, Gerb & Soffen, LLP

[57] ABSTRACT

Sensor devices for use in assaying for a ligand in a sample are described, the devices comprising: i) a discrete zone ("the measurement zone") on a region of which ("the measurement region") is immobilized directly or indirectly a first specific binding partner for the ligand under assay (or a reagent precomplexed with or capable of forming a complex with a specific binding partner for the ligand under assay), which zone additionally contains in releasable form, a first known amount of an optionally labelled second specific binding partner for the ligand under assay, the second specific binding partner being directed to an epitope of the ligand assay different to the epitope to which the first specific binding partner is directed; and ii) a second discrete zone ("the reference zone") on a region of which is immobilized directly or indirectly a first specific binding partner for the ligand under assay (or a reagent precomplexed with or capable of forming a complex with a specific binding partner for the ligand under assay), which zone additionally contains, in releasable form, a known amount of ligand analogue and separately contains, in releasable form, a second known amount of an optionally labelled second specific binding partner for the ligand under assay as defined above, said second known amount being less than the aforementioned first known amount in the measurement zone. Methods of sandwich assay using such devices are also described.

19 Claims, 4 Drawing Sheets

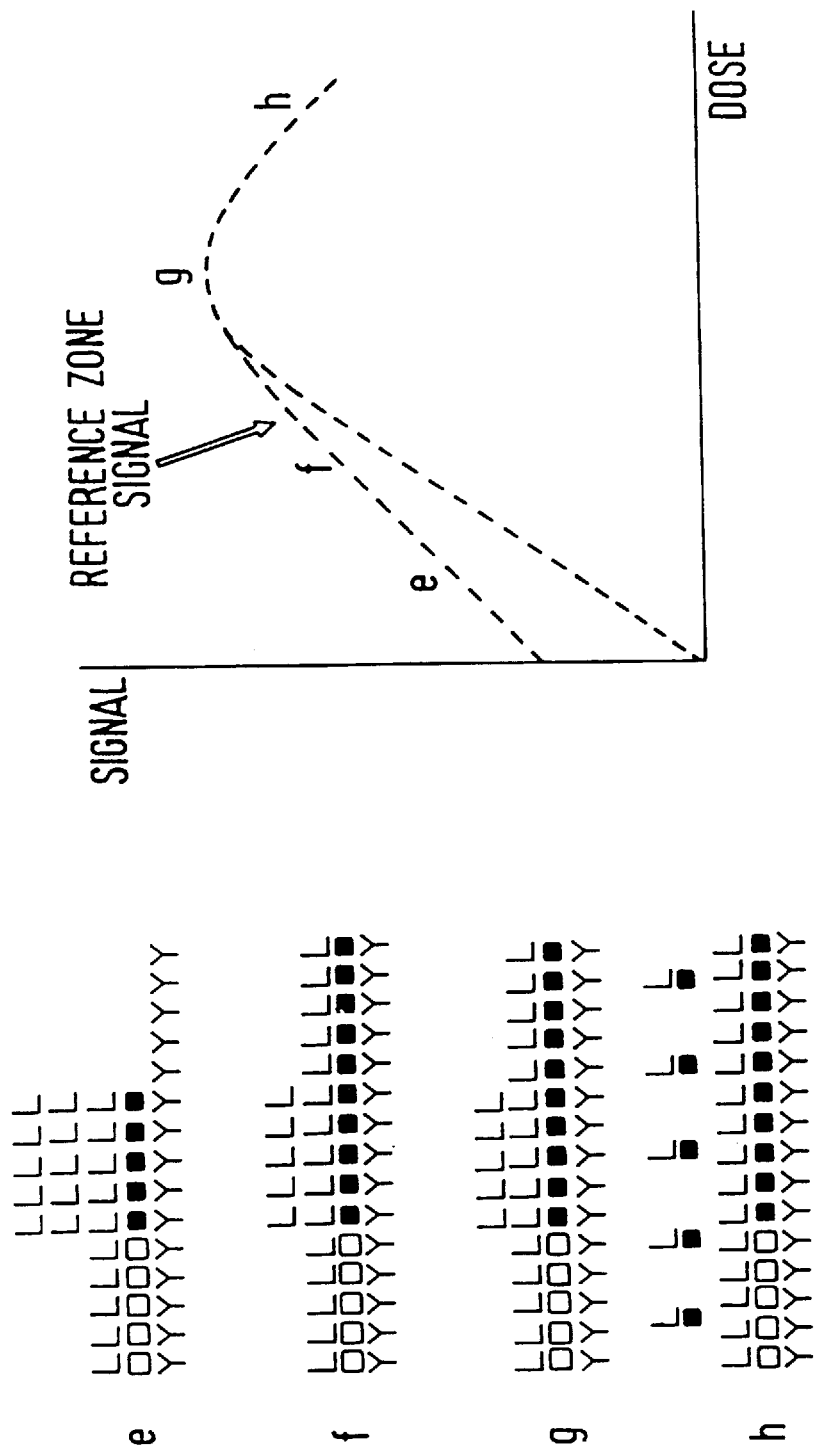

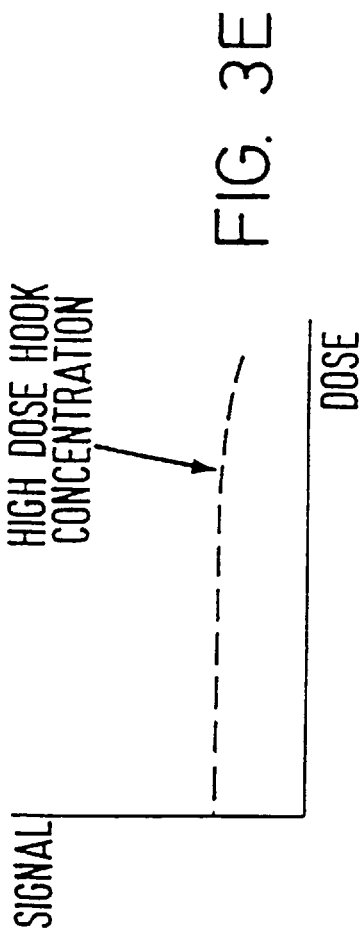
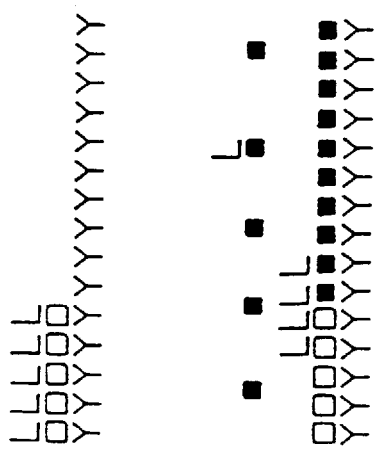

FIG. 4A
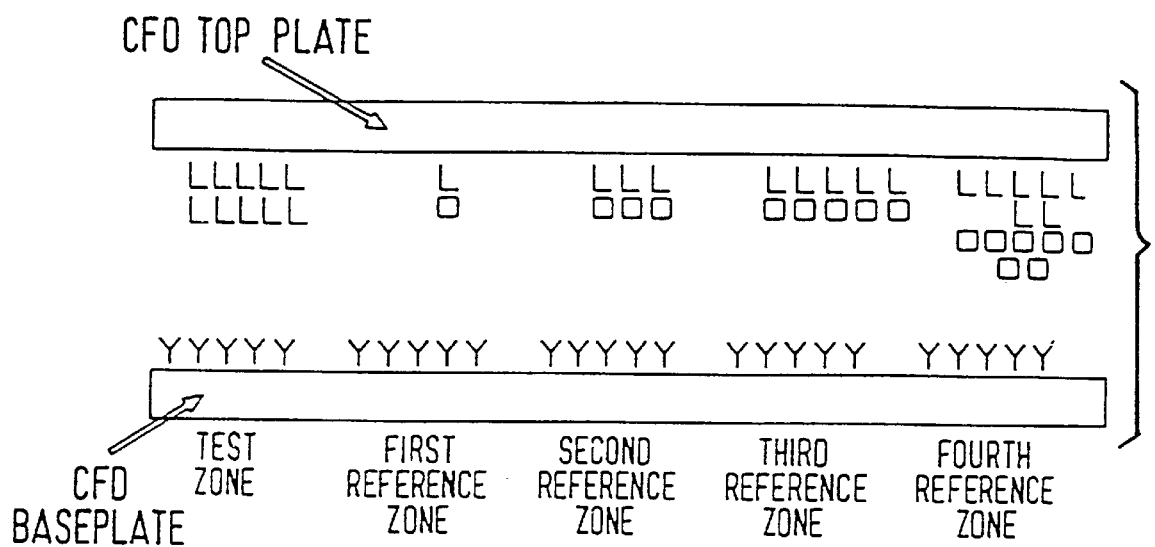
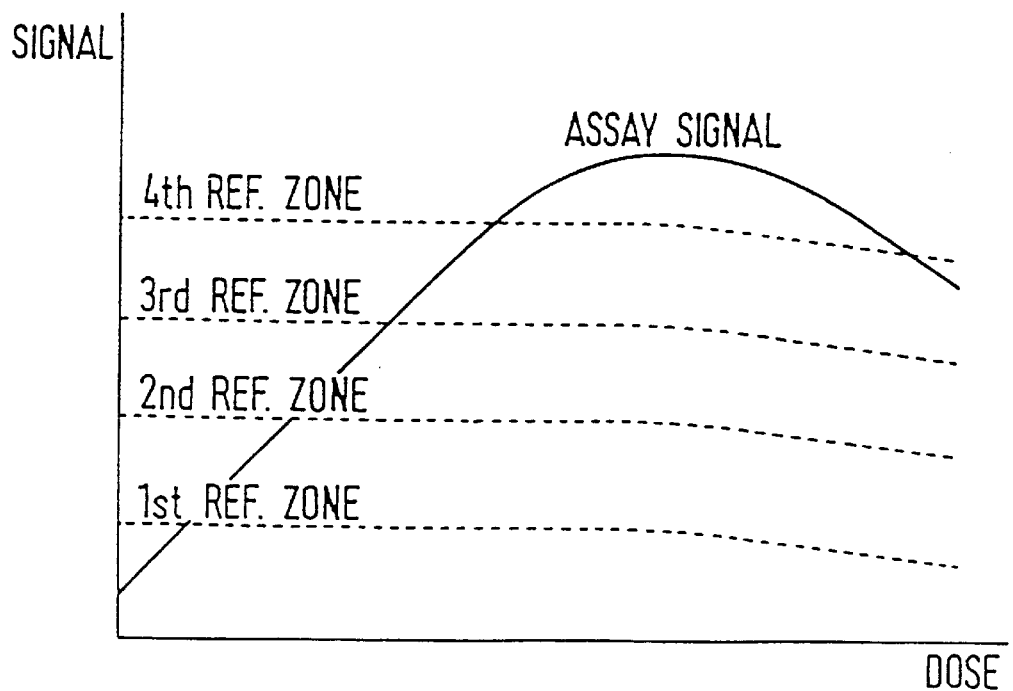
FIG. 4

SENSOR DEVICE FOR SANDWICH ASSAY

The present invention relates to a method of conducting sandwich assays of chemical, biochemical or biological entities and to devices for use in such a method.

There is a now a great interest in the development of assay devices and techniques for the detection and measurement of the presence of an analyte in a sample, and the various methods and devices available have been extensively reviewed, for example in Biosensors: Fundamentals and Applications, edited by A. P. F. Turner, I. Karube, G. S. Wilson, Oxford Scientific Publications, 1987. Standard assay techniques, however, are highly sensitive to a wide variety of conditions and interfering factors-which may affect the level of the signal observed e.g.temperature, reagent stability, incubation and development time. Accordingly, the analytical performance of standard assay techniques is often limited by the method of calibration of the immunosensor used, which usually involves carrying out an assay on a standard sample containing a known amount of analyte. In respect of assays which involve an antibody, the immunological binding reactions which occur are frequently irreversible. Thus any calibration steps need to be carried out using a separate device or devices (preferably from the same manufacturing batch) which inevitably introduces errors.

The need for a separate calibration step involving the use of additional sensing devices can be avoided by using in the assay a device which is provided with separate zones whereby the calibration step is effected within the assay procedure. Such methods applicable to both sandwich assays and competition assays are described in WO92/09892.

Standard sandwich assay techniques are particularly liable to exhibit the high dose 'hook' effect (a paradoxical reversal of the standard curve at high doses of analyte), a typical standard curve for a conventional immunoassay being illustrated in FIG. 1. This effect can be eliminated by using sequential rather than simultaneous application of the different specific binding partners for the analyte under assay. Alternatively, elimination of the high dose 'hook' effect necessitates assay of a sample at at least two different dilutions. The most usual way, however, of performing a one-step sandwich assay is to employ a large excess of the labelled specific binding partner to alleviate the high dose 'hook' effect.

An alternative to using excess labelled specific binding partner is to reference the sandwich assay by dosing a known amount of the analyte under assay into the assay device. In the absence of the analyte of interest in the sample, a fixed signal will be obtained, but when analyte is present the dose-response curve of the reference assay will be offset compared with that of the test assay, the relative magnitude of the offset decreasing with increasing analyte concentration. Eventually, however, at high analyte concentration the offset becomes zero as the immobilised specific binding partner is saturated with analyte. This is illustrated for an immunoassay in FIG. 2 and clearly, therefore, such referencing techniques will not be satisfactory at all concentrations of analyte present in the sample but especially at high analyte concentration and do not alleviate the high-dose hook effect.

In the sandwich assay techniques described in WO92/09892, one method of referencing employs a device having a reference zone containing an immobilised specific antibody to the antigen under assay, the reference zone also containing a pre-complexed mixture of a labelled second specific antibody to the antigen under assay and the antigen under assay. Although such a complex is likely to be more stable than the separate components it is, unfortunately, unable to mimic the performance of the second specific binding partner in the measurement zone of the device. There can be also be a further disadvantage with this type of referencing in that should the second specific antibody have degraded during manufacture or storage of the device, no information can be gained about its reactivity by interrogating the reference zone. We have now found that these disadvantages can be overcome if the specific antibody and antigen under assay are initially present in the device separately rather than being precomplexed.

We have now developed an assay device and a method of assay suitable for sandwich assays which overcome the problems of the known assay techniques and which offer means for calibrating the assay as part of the assay procedure.

Thus, according to a first aspect of the present invention there is provided a sensor device which comprises i) a discrete zone ("the measurement zone") on a region of which ("the measurement region") is immobilised directly or indirectly a first specific binding partner for the ligand under assay (or a reagent precomplexed with or capable of forming a complex with a specific binding partner for the ligand under assay), which zone additionally contains, in releasable form, a first known amount of an optionally labelled second specific binding partner for the ligand under assay, the second specific binding partner being directed to an epitope of the ligand under assay different to the epitope to which the first specific binding partner is directed; and ii) a second discrete zone ("the reference zone") on a region of which is immobilised directly or indirectly a first specific binding partner for the ligand under assay (or a reagent precomplexed with or capable of forming a complex with a specific binding partner for the ligand under assay), which zone additionally contains, in releasable form, a known. amount of ligand analogue and separately contains, in releasable form, a second known amount of an optionally labelled second specific binding partner for the ligand under assay as defined above, said second known amount being less than the aforementioned first known amount in the measurement zone.

The term "ligand analogue" is used to denote a species which is capable of binding to the same epitopic site of the same specific binding partner as the ligand under assay, and includes inter alia within its scope a known amount of ligand under assay.

The known amount of optionally labelled specific binding partner in the reference zone must be less than that in the measurement zone in order that the reference zone gives rise to a signal which is constant and independent of the amount of analyte present in the sample up to the high dose hook concentration for the assay.

The device according to the invention may also contain one or more additional reference zone(s), each reference zone present containing different known amounts of optionally labelled specific binding partner.

According to a further aspect of the present invention there is provided a method of assay for a ligand in a sample which comprises the steps of i) incubating the sample with a device according to the invention as hereinbefore defined;

ii) monitoring the signal appropriate to the assay technique employed arising from the measurement zone (as hereinbefore defined) of said device ("the assay signal");

iii) simultaneously or sequentially to the said monitoring in ii), monitoring the signal appropriate to the assay technique employed arising from the reference zone(s) (as hereinbefore defined) of said device ("the reference signal (s)"); and iv) comparing the reference signal(s) with the assay signal, thereby determining using an appropriate algorithm whether and/or the extent to which the ligand under assay is present in the sample.

The incubation in step i) involves contacting the sample with the measurement zone of said device and simultaneously or sequentially contacting the sample with the reference zone(s) of said device.

A wide variety of devices may be used to perform the method of the present invention, including, for example, dipstick or "test-strip" biosensors, a device using a "sample flow-through" configuration or devices employing sample containment. Examples of biosensors which may be used in the method of the present invention include sensors involving surface plasmon resonance, resonant mirror techniques, piezoelectric and total internal reflectance techniques.

However, a preferred device according to the present invention is a capillary fill device, especially a fluorescence capillary fill device, for example the type of device described in EP-A-171148 or in WO-90/14590. Such capillary fill devices may be used singly or in a suitable holder such as described in WO-90/1830

As described in EP-A-171148, a capillary fill device (hereinafter CFD) typically consists of two plates of transparent material, e.g. glass, separated by a narrow gap or cavity. One plate acts as an optical waveguide and carries an immobilised reagent appropriate to the test to be carried out in the device. As described in WO-90/14590, the other transparent plate can carry on its surface remote from the cavity a layer of light-absorbing or opaque material. For use in a sandwich assay, the immobilised reagent may, for example, be a specific binding partner to the ligand desired to be detected and either one of the plates may carry a soluble reagent comprising a further specific binding partner to the ligand under assay labelled with a fluorescent dye (the ancillary reagent). When a sample is presented to one end of the CFD, it is drawn into the gap by capillary action and dissolves the ancillary reagent. Because the capillary gap is narrow (typically about 100 $\mu$m), the binding reaction will generally go to completion in a short time, possibly less than 5 minutes depending on the sample matrix, type of assay and reagent affinities. In a sandwich immunoassay for an antigen, a sample antigen will form a sandwich complex with a fluorescently labelled antibody and an antibody immobilised on the waveguide. Thus, for a sandwich immunoassay, the amount of fluorescently labelled antibody which becomes indirectly bound to the waveguide by virtue of complex formation will, in general, be directly proportional to the concentration of antigen in the sample.

The term "antigen" as used herein will be understood to include both antigenic species, (for example, proteins, bacteria, bacterial fragments, cells, cell fragments and viruses) and haptens which may be rendered antigenic under suitable conditions.

Thus, according to a preferred embodiment of the device according to the present invention we provide a specifically-reactive sample-collecting and testing device for use in a sandwich assay for a ligand, possessing a cavity having two zones I and II mutually separated and each zone carrying a layer comprising, in releasable form, a reagent suitable for the desired assay, said surface being a surface of a first solid plate fashioned of transparent material, wherein the wall of the or each cavity opposite to said first plate comprises a second plate fashioned of transparent material and adapted to act as a light transmissive waveguide, the second plate having on its surface adjacent the cavity two zones IV and V corresponding in orientation to the aforementioned zones I and II respectively, each of zones IV and V carrying a layer comprising an immobilised reagent suitable for the desired assay. The first plate advantageously carries on its external face an opaque coating.

The arrangement of the aforementioned zones is such that zone I is paired together with zone IV and zone II is paired together with zone V, such that one of said pairs provides the measurement zone as defined hereinbefore and the other pair provides the reference zone as defined hereinbefore.

As mentioned earlier, CFDs and other devices according to the invention may, if desired, contain more than one reference zone; and may if desired contain multiple measurement zones enabling simultaneous or sequential assays for ligands in the same sample to be conducted. For example, the device could contain a measurement zone and two or three reference zones as herein defined for the same assay, to improve the accuracy of the calibration of the assay. Alternatively, the device could contain a first measurement zone and a reference zone as herein defined for one assay together with a further measurement zone for a different assay; the reference zone would also serve as a calibration for the further measurement zone although such calibration would differ from that for the measurement zone.

The reagents carried in the zones on the first transparent plate may be contained within a dissoluble layer of a suitable material. After deposition of the soluble reagent, a capping layer e.g. polyvinyl alcohol (PVA) may be placed upon the reagent, which capping layer delays the dissolution of the reagent for a few seconds after the addition of the sample to the device. This is to prevent the reagents being washed from one zone to another thereby precluding an accurate assay. The cavity or cavities of the device are preferably of a dimension small enough to enable sample liquid to be drawn into the cavity by capillary action, although any other method of filling said cavities may be employed. The zones on the first transparent plate and thereby the corresponding zones on the second transparent plate may be arranged either in tandem or in any other geometrical arrangement which maintains the integrity of the zones.

The capillary fill devices according to the invention may be manufactured by methods broadly similar to those described in EP-A-171148. According to a further aspect of the present invention, we also provide a method of manufacturing specifically-reactive sample-testing devices as described hereinbefore, comprising the steps of (a) forming an array of patches of suitable reagents, carried by zones I and II as described hereinbefore on the surface of a sheet material which is to provide part of a multiplicity of the devices, (b) forming an array of patches of suitable reagents, carried by zones IV and V as described hereinbefore on the surface of an additional structure, involving, where appropriate the immobilisation of specifically reactive species as described hereinbefore, said additional structure together with the said sheet material providing for each of the multiplicity of devices a cavity for collecting and retaining a volume of sample liquid in contact with the said layers of suitable reagents, the cavity preferably being of capillary dimension, and (c) separating the sheet material into portions each providing one or a plurality of the sample-collecting and testing devices.

In this process, the zones of reagents contained on the first plate may be continuous if the reagents contained in the zones are of an identical nature. Alternatively, the zones of reagents contained on the first plate, like the zones of reagents contained on the second plate, may be divided into a pattern of discrete portions, for example as a two-dimensional array of patches. When such patches are formed, they can be made, for example, by firstly forming a continuous layer and then removing portions thereof to leave the desired pattern of identical reagent patches. Alternatively the desired pattern of patches may be applied directly by any conventional printing method (for example by ink-jet printing or screen-printing), such a technique being most applicable to embodiments where, for each of the aforementioned plates, the reagents contained in the zones on said plate are not identical in nature or else are very expensive and their usage has to be kept to a minimum. Ink-jet printing is the preferred method of applying the reagents.

The immobilisation of a specifically reactive species onto the surface of the cavity may be carried out directly or indirectly. For example, when the specifically reactive species is an antibody, indirect immobilisation may be effected by means of an antispecies antibody which is itself bound to the said surface. Alternatively, immobilisation may be effected by conjugating an antibody with biotin and complexing with avidin pre-immobilised on the said surface; or vice versa. A further example of indirect immobilisation involves conjugating fluorescein isothiocyanate (FITC) to the specific binding partner for the species under assay and immobilising anti-FITC antibody onto said surface. Direct immobilisation may be effected by activating the said surface by treatment with a suitable reagent (e.g. a silanisation reagent such as aminopropyltrimethoxy-silane) to which the antibody can be covalently coupled using an appropriate cross-linking reagent (e.g. glutaraldehyde or glycolaldehyde). Alternative techniques well-known to the man skilled in the art may be used for immobilization of the said coating. Haptens and antigens may be immobilised directly onto the surface of the cavity by using appropriate immobilisation chemistry. Alternatively, these haptens and antigens may be conjugated to a protein e.g. poly-L-lysine and then immobilised via the protein onto the cavity surface using known methods.

The mode of operation of one embodiment of the method according to the invention will now be described in terms of an immunoassay of an antigenic species. The assay signal is determined by contacting the sample with an immobilised first specific antibody to the antigen under assay and a fluorescently labelled second specific antibody to the antigen under assay. The amount of labelled antibody which becomes bound in the measurement region as a result of an immunological reaction can be determined by standard methods and this amount can be related to the amount of antigen in the sample. The calibration of the assay is carried out by contacting the sample with an immobilised first antibody to the antigen under assay and with a non-precomplexed combination of a known amount of labelled specific second antibody to the antigen under assay and a known amount of antigen. When there is no analyte present in the sample, the reagents in the reference zone give rise to a signal resulting from the known amount of labelled antibody in the reference zone since all the labelled antibody will become bound to the baseplate as a result of the immunological reaction involving the known amount of antigen. As the analyte concentration in the sample increases, the known amount of labelled antibody will still bind to the immobilised reagent in the reference zone resulting in a signal which remains equivalent to that which arises when no analyte is present because of the fixed amount of labelled antibody in the reference zone, i.e. the signal arising from the reference zone will be independent of the total concentration of antigen in the device. When the concentration of antigen in the sample is equivalent to that which results in an assay signal of a value of the high-dose hook region of the assay curve some labelled antibody in the reference zone will bind to antigen bound to the immobilised antibody and some will bind to antigen which remains free in solution. Accordingly, this will result in a decrease in the signal arising from the reference zone enabling the user to know that the concentration of analyte present in the sample is greater than the high-dose hook concentration. This embodiment and the resulting signals obtained are illustrated in FIG. 3.

The sandwich assay method according to the present invention provides the following specific advantages:

i) The reagents used in the reference zone are equivalent to those used in the measurement zone and they will therefore perform in the same manner, i.e. they will respond similarly in both zones to variations in their environment, ii) In the reference zone, the (labelled) specific binding partner and the ligand analogue are separate i.e. they are not pre-complexed. Accordingly, it is possible to gain information about the quality of the specific binding partner (and its label), i.e. information as to whether it has degraded during manufacture or storage of the device by suitable interrogation of the reference zone.

iii) There is a means to warn the operator that the concentration of analyte in the sample is very high and that the sample may, for example, therefore need to be diluted and re-assayed, namely the decrease in the signal from the reference zone at high analyte concentration.

iv) Should there be endogenous interfering factors in the sample (e.g. for an immunoassay where one of the specific binding partners is a polyclonal antibody the presence of antibodies such as, for example, human antimouse antibodies (HAMA)), then the reference zone will be influenced in the same way as the measurement zone. The reference zone can therefore be used to either correct for such interference or to alert the operator to its existence.

A further advantage arises where a plurality of reference zones are employed, each reference zone containing different amounts of labelled specific binding partner and ligand analogue The signals arising from each of the reference zones will correspond to different dose values on the measurement zone assay dose/response curve and this will therefore allow for full quantification of the assay. In particular, the reference zones can be constructed to give information about the middle region of the assay curve, this region often being the most useful region for an assay determination. An illustration of a CFD containing four reference zones, and the signals which would arise from these zones as related to that from the assay zone is illustrated in FIG. 4.

Although the embodiments described hereinbefore illustrate the method of the invention to be particularly applicable to immunoassays, and in the preferred embodiments of the invention the ligand is a antigen and the specific binding partner comprises an antibody to the said antigen, the invention is not to be taken as limited to assays of antibodies or antigens. Examples of ligands which may be assayed by the method of the invention are given in Table 1 below, together with an indication of a suitable specific binding partner in each instance.

In FIGS. 1 to 4 the symbols illustrated denote the following entities:

Y—Capture antibody
L—Labelled second antibody
■—Sample antigen
☐—Antigen dosed into the assay device FIG. 1 shows a typical standard curve for a conventional immunoassay.

FIG. 2 shows a dose-response curve.

FIG. 3 shows a dose-response curve.

FIG. 4 shows an embodiment of the disclosed sensor having four reference zones and a dose-response curve of signals measured with this embodiment.

TABLE 1

Figure 1:
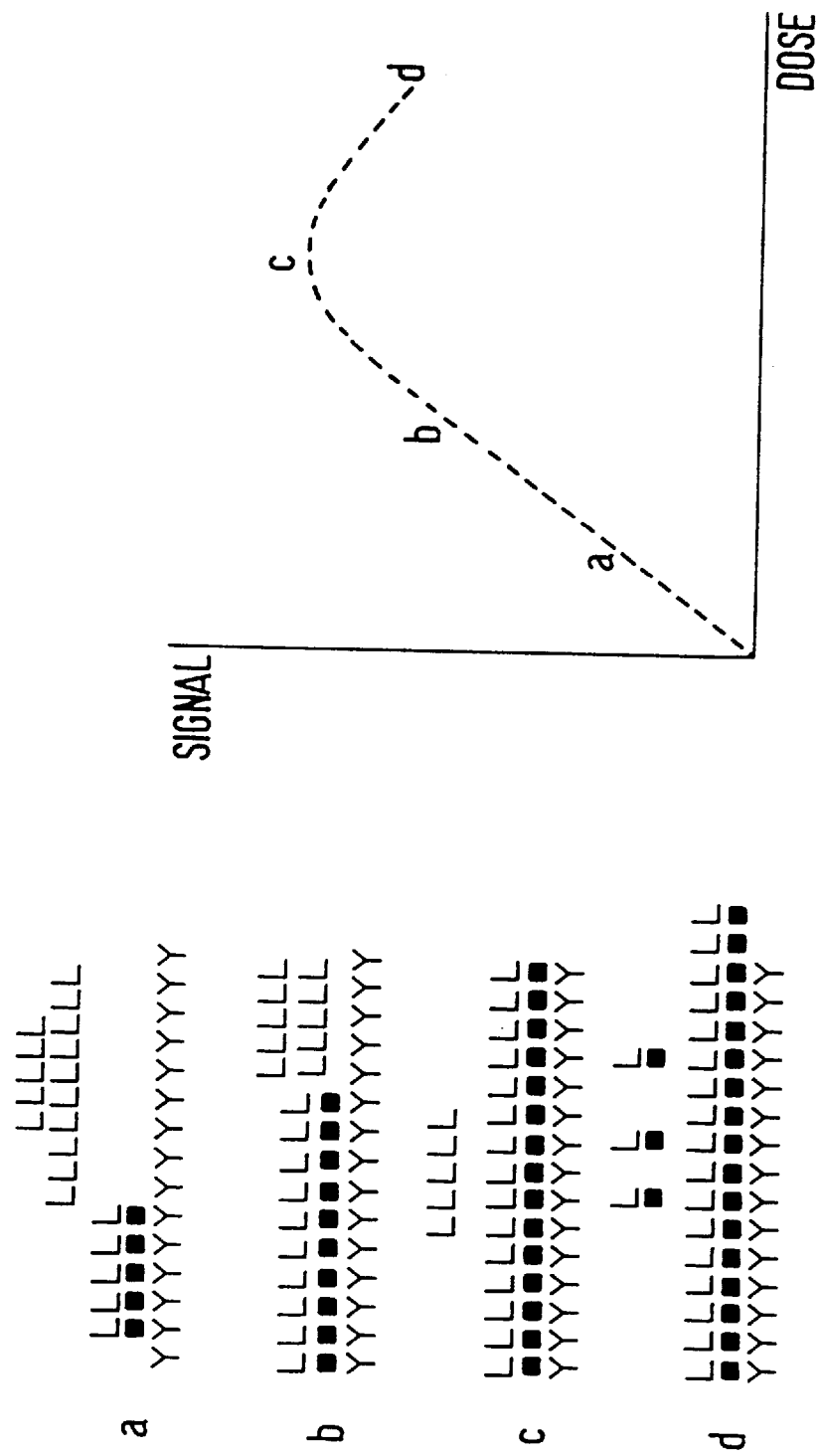

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| protein A | immunoglobulin |
| immunoglobulin | protein A |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinizing hormone (LH), human chorionic gonadotrophin (hCG), follicle stimulating hormone (FSH), insulin and prolactin) or non-peptide hormones, or thyroid hormones), proteins (e.g. carcinoembryonic antigen (CEA) and alphafetoprotein (AFP)), sugars, toxins, vitamins, proteins, viruses such as influenza, para-influenza, adeno virus, hepatitis, respiratory and AIDS viruses, or microorganisms.

It will be understood that the term "antibody" used herein includes within its scope:

(a) any of the various classes or sub-classes of immunoglobulin, e.g. IgG, IgA, IgM, or IgE derived from any of the animals conventionally used, e.g. sheep, rabbits, goats or mice, (b) monoclonal antibodies, (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or the so-called "half-molecule" fragments obtained by reductive cleavage of the disulphide bonds connecting the heavy chain components in the intact antibody, (d) antibodies or antibody fragments produced or modified by recombinant DNA techniques.

The method of preparation of fragments of antibodies is well known in the art and will not be described herein.

As indicated above, various reagents may be optionally labelled. As examples of species for use as labels in the method according to the present invention are included fluorophores, enzymes, high refractive index particles and other species well known to the man skilled in the art. Preferably, fluorophores are used as labels. Examples of suitable fluorophores include fluorescein and its derivatives (e.g. fluorescein isothiocyanate (FITC)), rhodamine and its derivatives (e.g. XRITC, TRAP, TRITC), lucifer yellow, 2,4-dinitrofluorobenzene, phenylisothiocyanate, dansyl chloride, phycobiliproteins (e.g. allophycocyanin and phycoerythrin) and indocyanins.

It is also be advantageous to provide for additional compensation for various factors in the assay system which may influence the level of signal observed. Current assay techniques are highly sensitive to temperature, reagent stability, incubation and development time and other conditions and interfering factors which may affect the level of signal observed. This additional compensation can be achieved, for example, by using an assay method as hereinbefore described in which additional separate calibration step(s) are carried out. In such a method, a device is used which is provided with appropriate reagents disposed in one or more zone(s) (calibration zone(s)) separate from the measurement zone and reference zone. The concept of using calibration zones for such compensation is described in detail in WO92/09892.

The use of such calibration step(s) will serve two main purposes, namely i) to confirm that the various reagents used in the assay procedure are performing according to their specification, and ii) to define a certain concentration level within the sample under test, and thereby to compensate for background fluorescent levels, temperature and pH changes and other factors which may alter the level of the observed signals.

Alternatively, an additional calibration zone may be employed for compensating for "edge effects" as described in International Patent Application No. PCT/GB93/01217.

Thus according to a further aspect of the present invention, we provide a device for use in an assay in which one or more additional calibration step(s) are carried out being a device as hereinbefore defined additionally comprising one or more further discrete zone(s) ("the calibration zone(s)") on a region of which is immobilised directly or indirectly a reagent ("the calibration reagent") appropriate to the assay technique employed, which zone may also contain appropriate ancillary reagents suitable for the desired assay.

Thus, according to a further aspect of the present invention, there is provided a method of assay for a ligand in a sample as hereinbefore defined, additionally comprising the steps of v) simultaneously or sequentially to the incubation in step i), incubating the sample, if desired together with one or more ancillary reagents, with the calibration zone(s) of a device as hereinbefore defined;

vi) monitoring the signal(s) ("the calibration signal(s)") appropriate to the assay technique employed arising from the calibration zone(s); and vii) subsequently comparing the calibration signal(s) to both the assay signal and the reference signal as hereinbefore defined and, using an appropriate algorithm, the measure of the extent to which the ligand under assay is present in the sample, as derived from the assay signal and the reference signal, is thereby calibrated.

Manufacture of devices possessing a plurality of reference zones and/or one or more calibration regions as described above may be carried out by an analogous method to that described hereinbefore for devices possessing only zones I and II, by additionally forming the patch of suitable reagents in the further zone(s) on the surface of the sheet material and immobilising the suitable reagents in the further zone(s) on the surface of the additional structure.

Where more than one calibration and/or reference zone is present, the reagents on each will generally be chosen such that the signals arising from each zone are not identical. Such non-identical signals can arise where the signal arising from each zone is the same function of the amount of ligand present in the sample. One example is where the calibration reagents in each calibration zone are the same but the amounts of ancillary reagent(s) which form a complex with the calibration reagents in each zone differ. Another example is where the calibration reagents in each calibration zone each give rise to a signal without the need for an ancillary reagent and are present in differing amounts. If it is found, despite such a choice of calibration reagents that identical signals arise, then device failure (e.g. due to extremes of sample pH, too high a sample background signal, reagent degradation or interference in the assay by a factor in the sample) is indicated and the assay can be rejected; this is a further advantage of the present invention.

Thus, the reagents used in the calibration zone(s) are chosen so as to give rise to a zero or non-zero signal for the purposes of additional calibration of the assay. The term "zero signal" denotes the background signal for the assay concerned. The term "non-zero signal" is to be construed accordingly. In a sandwich assay the zero signal will be the signal obtained when no analyte is present.

Various methods may be used to calibrate the assay signal by means of the calibration signal(s). These methods can be summarised as either an additive, multiplicative or a combined additive/multiplicative method. All methods rely on characterisation of the calibration region(s) during manufacture, so that any difference measured at the time of assay can be used to correct the data from the measurement region.

In a sandwich assay according to a further embodiment of the present invention in which one or more additional calibration step(s) are carried out as hereinbefore described, in step v) either a) the calibration reagent (or optionally an ancillary reagent precomplexed with or capable of forming a complex involving the calibration reagent) is a specific binding partner for the ligand under assay, a labelled specific binding partner for the ligand under assay is present as an ancillary reagent and a known amount of the ligand under assay precomplexed to its labelled specific binding partner is present as a yet further ancillary reagent or b) a labelled specific binding partner for the ligand under assay is present as an ancillary reagent and the calibration reagent (or optionally an ancillary reagent precomplexed with or capable of forming a complex involving the calibration reagent) is a known amount of the ligand under assay precomplexed to its immobilized specific binding partner or c) a ligand distinct from the ligand under assay is present as an ancillary reagent and the calibration reagent (or optionally an ancillary reagent precomplexed with or capable of forming a complex involving the calibration reagent) is a labelled specific binding partner for the ligand distinct from the ligand under assay or d) the calibration reagent is a labelled binding partner nonspecific for any ancillary reagent(s) present or e) the calibration reagent gives rise to the desired signal without the need for the presence of an ancillary reagent.

A wide range of possibilities present themselves for the configuration of the calibration regions for use in the method of the present invention. These possibilities are set out in detail in WO92/09892 incorporated herein by reference.

Thus according to a further aspect of the present invention, we provide a device for use in an assay in which one or more additional calibration step(s) are carried out as hereinbefore described, being a specifically-reactive sample-collecting and testing device as defined hereinbefore additionally carrying on said first plate one or more further zone(s) carrying a layer comprising, in soluble releasable form, ancillary reagent(s) suitable for the desired assay and additionally carrying on said second plate one or more further zone(s) each of which is corresponding in orientation to one of said further zone(s) on said first plate, and each of which is carrying a layer comprising an immobilised calibration reagent as hereinbefore defined.

The present invention further provides apparatus suitable for use in the method of assay according to the present invention as hereinbefore described which comprises a device according to the invention as hereinbefore defined; and means for generating and monitoring the signals from the device.

We claim:

1. A sensor device for use in a sandwich assay for a ligand in a sample which comprises i) a first discrete measurement zone having a region on which is immobilised directly or indirectly a first specific binding partner for the ligand under assay or a reagent precomplexed with or capable of forming a complex with a specific binding partner for the ligand under assay, which measurement zone additionally contains, in releasable form, a first known amount of labelled second specific binding partner for the ligand under assay, the second specific binding partner being directed to an epitope of the ligand under assay different to the epitope to which the first specific binding partner is directed; and ii) a second discrete reference zone having a region on which is immobilised directly or indirectly a first specific binding partner for the ligand under assay or a reagent precomplexed with or capable of forming a complex with a specific binding partner for the ligand under assay, which reference zone additionally contains, in releasable form, a known amount of ligand analogue and separately contains, in releasable form, a second known amount of a labelled second specific binding partner for the ligand under assay, said second known amount being less than the aforementioned first known amount in the measurement zone.

2. A device as claimed in claim 1 also containing one or more additional reference zone(s), each reference zone present containing different known amounts of said labelled second specific binding partner.

3. A device as claimed in claim 1 wherein the device is a capillary-fill device containing said first and second zones.

4. A device for use in a sandwich assay for a ligand in a sample in which one or more additional calibration step(s) are carried out being a device as claimed in claim 1 additionally comprising one or more further discrete calibration zone(s) having a region on which is immobilised directly or indirectly a calibration reagent appropriate to the assay.

5. A device as claimed in claim 1 being a specifically-reactive sample-collecting and testing device for use in a sandwich assay for a ligand, possessing a cavity having two regions I and II mutually separated and each region carrying a layer comprising, in releasable form, a reagent suitable for the desired assay, said regions on which said layers are carried having a surface of a first solid plate fashioned of transparent material, wherein the wall of the or each cavity opposite to said first plate comprises a second plate fashioned of transparent material and able to act as a light transmissive waveguide, the second plate having on its surface adjacent the cavity two regions IV and V corresponding in orientation to the aforementioned regions I and II respectively, each of regions IV and V carrying a layer comprising an immobilised reagent suitable for the desired assay, said regions being arranged such that region I is paired with region IV and region II is paired with region V such that one of said pairs provides the measurement zone and the other pair provides the reference zone.

6. A device as claimed in claim 5, being a specifically-reactive sample-collecting and testing device additionally carrying on said first plate one or more further region(s) carrying a layer comprising, in soluble releasable form, ancillary reagent(s) suitable for the desired assay and additionally carrying on said second plate one or more further region(s) each of which is corresponding in orientation to one of said further region(s) on said first plate, and each of which is carrying a layer comprising an immobilised calibration reagent.

7. A device as claimed in claim 5 wherein the first plate carries on its surface remote from the cavity a layer of light-absorbing or opaque material.

8. A method of sandwich assay for a ligand in a sample which comprises the steps of
   i) incubating the sample with a device as claimed in claim 1,
   ii) monitoring a signal appropriate to the assay arising from the measurement zone of said device,
   iii) simultaneously or sequentially to the said monitoring in ii), monitoring a signal appropriate to the assay arising from the reference zone(s) of said device; and
   iv) comparing the signal(s) from the reference zone with the signal from the assay zone, thereby determining using an appropriate algorithm whether and/or the extent to which the ligand under assay is present in the sample.

9. A method of sandwich assay for a ligand in a sample in which one or more additional calibration step(s) are carried out, being a method as claimed in claim 8 wherein in step i) the sample is incubated in the presence of the device additionally carrying on a first plate one or more further zone(s) carrying a layer comprising, in soluble releasable form, ancillary reagent(s) suitable for the desired assay and additionally carrying on a second plate one or more calibration zone(s) each of which is corresponding in orientation to one of said further zone(s) on said first plate, and each of which is carrying a layer comprising an immobilised calibration reagent, said method additionally comprising the steps of
   v) simultaneously or sequentially to the incubation in step i), incubating the sample, if desired together with one or more ancillary reagents, with the calibration zone(s) of the device;
   vi) monitoring signal(s) appropriate to the assay arising from the calibration zone(s); and
   vii) subsequently comparing the signal(s) from the calibration zone to both the signal from the assay zone and the signal from the reference zone and, using an appropriate algorithm, the measure of the extent to which the ligand under assay is present in the sample, as derived from the signals is thereby calibrated.

10. A method as claimed in claim 9 wherein, in step v) either a) the calibration reagent (or optionally an ancillary reagent precomplexed with or capable of forming a complex involving the calibration reagent) is a specific binding partner for the ligand under assay, a labelled specific binding partner for the ligand under assay is present as an ancillary reagent and a known amount of the ligand under assay precomplexed to its labelled specific binding partner is present as a yet further ancillary reagent or b) a labelled specific binding partner for the ligand under assay is present as an ancillary reagent and the calibration reagent (or optionally an ancillary reagent precomplexed with or capable of forming a complex involving the calibration reagent) is a known amount of the ligand under assay precomplexed to its immobilized specific binding partner or c) a ligand distinct from the ligand under assay is present as an ancillary reagent and the calibration reagent (or optionally an ancillary reagent precomplexed with or capable of forming a complex involving the calibration reagent) is a labelled specific binding partner for the ligand distinct from the ligand under assay or d) the calibration reagent is a labelled binding partner non-specific for any ancillary reagent(s) present or e) the calibration reagent gives rise to the desired signal without the need for the presence of an ancillary reagent.

11. A method of manufacturing a specifically-reactive sample-testing device as claimed in claim 5, comprising the steps of
   (a) forming an array of patches of suitable reagents, carried by zones I and II as defined in claim 5 on the surface of a sheet material which is to provide part of a multiplicity of the devices,
   (b) forming an array of patches of suitable reagents, carried by zones IV and V as defined in claim 5 on the surface of an additional structure, involving, where appropriate the immobilisation of said reagents, said additional structure together with the said sheet material providing for each of the multiplicity of devices a cavity for collecting and retaining a volume of sample liquid in contact with the said layers of suitable reagents, and
   (c) separating the sheet material into portions each providing one or a plurality of the sample-collecting and testing devices.

12. A method for the manufacture of a device as claimed in claim 11 in which said device additionally comprises on said first plate on or more further region(s) carrying a layer comprising, in soluble releasable form, ancillary reagent(s) suitable for the desired assay and additionally carrying on said second plate one or more further region(s) each of which is juxtaposed to one of said further region(s) on said first plate, and each of which is carrying a layer comprising an immobilised calibration reagent, and said method additionally comprising the steps of forming the patch of reagents in the further region(s) on the surface of the sheet material and immobilising the reagents in the further region(s) on the surface of the additional structure.

13. Apparatus suitable for use in a method of assay which comprises a device as claimed in claim 1; and means for generating and monitoring the signals from the device.

14. A device as claimed in claim 2, being a capillary device comprising two plates of transparent material in which a sample presented to one end of the device is drawn into the cavity between said plates by capillary action, wherein the immobilised and releasable reagents of said discrete measurement zone are juxtaposed on opposite surfaces of said plates and the immobilised and releasable reagents of said discrete reference zone are juxtaposed on opposite surfaces of said plates.

15. A device for use in a sandwich assay for a ligand in a sample in which one or more additional calibration step(s) are carried out being a device as claimed in claim 2 additionally comprising one or more discrete calibration zone(s) having a region on which is immobilised directly or indirectly a calibration reagent appropriate to the assay.

16. A device as claimed in claim 2 being a specifically-reactive sample-collecting and testing device for use in a sandwich assay for a ligand, possessing a cavity having two regions I and II mutually separated and each region carrying a layer comprising, in releasable form, a reagent suitable for the desired assay, said regions on which said layers are carried having a surface of a first solid plate fashioned of transparent material, wherein the wall of the or each cavity opposite to said first plate comprises a second plate fashioned of transparent material and able to act as a light transmissive waveguide, the second plate having on its surface adjacent the cavity two regions IV and V corresponding in orientation to the aforementioned regions I and II respectively, each of regions IV and V carrying a layer comprising an immobilised reagent suitable for the desired assay, said regions being arranged such that region I is paired with region IV and region II is paired with region V such that one of said pairs provides the measurement zone and the other pair provides the reference zone.

17. A device as claimed in claim 16, being a specifically-reactive sample-collecting and testing device additionally carrying on said first plate one or more further region(s) carrying a layer comprising, in soluble releasable form, ancillary reagent(s) suitable for the desired assay and additionally carrying on said second plate one or more further region(s) each of which is corresponding in orientation to one of said further region(s) on said first plate, and each of which is carrying a layer comprising an immobilised calibration reagent.

18. A device as claimed in claim 17 wherein the first plate carries on its surface remote from the cavity a layer of light-absorbing or opaque material.

19. A device as claimed in claim 18, being a capillary device comprising two plates of transparent material in which a sample presented to one end of the device is drawn into the cavity between said plates by capillary action, wherein the immobilised and releasable reagents of said discrete measurement zone are juxtaposed on opposite surfaces of said plates and the immobilised and releasable reagents of said discrete reference zone are juxtaposed on opposite surfaces of said plates.

* * * * *